United States Patent [19]
Cognacq

[11] 3,937,832
[45] Feb. 10, 1976

[54] ESTERS OF 2,2-DIPHENYL-CYCLOPROPANE-CARBOXYLIC ACIDS AS COUGH SUPPRESSANTS

[75] Inventor: Jean-Claude Cognacq, Bourg-la-Reine, France

[73] Assignee: Societe anonyme dite: Hexachimie, Malmaison, France

[22] Filed: Mar. 4, 1974

[21] Appl. No.: 448,033

Related U.S. Application Data

[62] Division of Ser. No. 214,473, Dec. 30, 1971, Pat. No. 3,846,436.

[52] U.S. Cl................................ 424/267; 424/274
[51] Int. Cl.² ...................................... A61K 31/445
[58] Field of Search......................... 424/267, 274

[56] References Cited
UNITED STATES PATENTS 3,317,526   5/1967   Dahlbom ............................ 260/469

OTHER PUBLICATIONS

Hager et al., J. Am. Pharm. Assoc. 41 pp. 193–96 (1952).
Weston, J.A.C.S. 68 2345–2348 (1946).
J. Pharm. & Exp. Therapeutics 96 42 (1949) Kratz et al.
Wilson et al., Textbook of Organic Medicinal and Pharmaceutical Chemistry p. 443.

*Primary Examiner*—Norman A. Drezin
*Attorney, Agent, or Firm*—Armstrong, Nikaido and Wegner

[57] ABSTRACT

The invention provides novel aminoethyl esters of 2,2-diphenylcyclopropane carboxylic acids which are anti-tussive agents.

14 Claims, No Drawings

ESTERS OF 2,2-DIPHENYL-CYCLOPROPANE-CARBOXYLIC ACIDS AS COUGH SUPPRESSANTS

This is a division of application Ser. No. 214,473 filed Dec. 30, 1971.

The present invention provides esters of 2,2-diphenyl-cyclopropane-carboxylic acids having the formula:

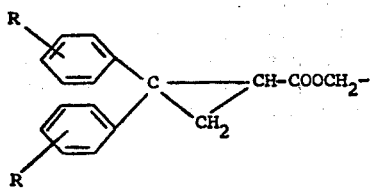

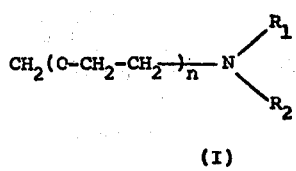

(I)

in which R is hydrogen, halogen, lower alkyl or lower alkoxy, n is zero or 1, and $R_1$ and $R_2$ which may be the same or different each denote an alkyl radical or $R_1$ and $R_2$ are joined together and, with the nitrogen atom to which they are attached, form a 5- to 7-membered heterocyclic ring which can contain another heteroatom in addition to the nitrogen, provided that, if $n$ is 0, $R_1$ and $R_2$ are not ethyl, and the salts of these esters with non-toxic acids. Preferably, $R_1$ and $R_2$ each denote a lower alkyl radical. Also preferred are compounds in which $R_1$ and $R_2$, together with the nitrogen atom to which they are attached, form a pyrrolidono, piperidino, lower alkyl-substituted piperidino, morpholino, perhydroazepino, piperazino, or N-(lower alkyl)-piperazino. The term "lower alkyl" denotes an alkyl radical having at most 4 carbon atoms.

The invention also provides a process for the preparation of the compounds of formula I, which comprises reacting a metal salt, preferably the sodium or potassium salt, of a 2,2-diphenyl-cyclopropane-carboxylic acid with a compound of general formula:

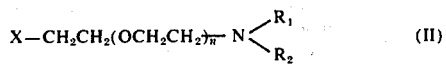
(II)

in which X represents chlorine, bromine or iodine, and $R_1$, $R_2$ and n are as defined above. The reaction is carried out in an alcoholic solvent, preferably ethanol or isopropanol, at the boiling point of the said solvent.

Another process according to the present invention comprises reacting a 2,2-diphenyl-cyclopropane-carboxylic acid chloride with an amino-alcohol of formula:

$$HO-CH_2CH_2(OCH_2CH_2)_{n}-N\begin{matrix}R_1\\R_2\end{matrix}$$ (III)

in which $R_1$, $R_2$ and $n$ are as defined above. The reaction can be carried out in an organic solvent such as diethyl ether, tetrahydrofuran, benzene, toluene, xylene, dimethylformamide or N-methyl-pyrrolid-2-one. The amino-alcohol (III) may be converted initially into its metal derivative, preferably into its sodium or potassium derivative. If the amino-alcohol is not converted into its metal derivative, the reaction is carried out in the presence of a tertiary amine such as triethylamine.

The compounds according to the invention display valuable pharmacological properties, in particular a marked anti-tussive action.

The following Examples illustrate the invention.

EXAMPLE 1

β-Piperidino-ethyl ester of 2,2-diphenyl-cyclopropane-carboxylic acid

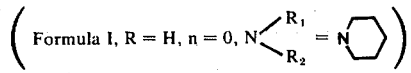

100 ml. of isopropanol and 0.21 mol of powdered sodium hydroxide are added to a mixture of 0.1 mol of 2,2-diphenyl-cyclopropane-carboxylic acid and 0.11 mol of piperidino-β-chloroethane hydrochloride. The mixture is heated under reflux for 8 hours, 300 ml. of water are added and the mixture extracted with diethyl ether. The ether phase is washed with water, dried over sodium sulphate, and the ether removed in vacuo to yield the base.

Preparation of the hydrochloride

A solution of hydrogen chloride in diethyl ether is added dropwise, with stirring, to a solution of the crude base in 100 ml. of diethyl ether, until the pH reaches 1. The mixture is triturated, and the product crystallises out. It is filtered off, washed with diethyl ether, dried and recrystallised from isopropanol. The hydrochloride thus obtained, on rapid heating melts at 178°–80°C; yield 78%.

Analysis $C_{23}H_{28}ClNO_2$, N% calculated 3.63; found 3.67.

EXAMPLE 2

2-(2'-pyrrolidino-ethoxy)-ethyl ester of 2,2-diphenyl-cyclopropane carboxylic acid

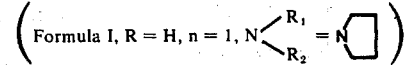

A solution of 0.1 mol of 2-(2'-pyrrolidino-ethoxy)ethanol in 30 ml. of anhydrous toluene is added dropwise to 0.1 mol of sodium hydride in 20 ml. of anhydrous toluene. The mixture is allowed to cool and then stirred for 1 hour at ambient temperature. A solution of 0.1 mol of 2,2-diphenyl-cyclopropane-carboxylic acid chloride in 30 ml. of anhydrous toluene is then added dropwise. When cool, the mixture is stirred for 2 hours at ambient temperature. 300 ml. of water are added and the mixture extracted with diethyl ether. The extract is dried over sodium sulphate, and the solvent is removed in vacuo to yield the base.

Preparation of the citrate

A solution of 0.1 mol of crude base in 250 ml. of diethyl ether is added dropwise, with stirring, to 0.1 mol of citric acid in 80 ml. of isopropanol. The mixture is stirred for 1 hour at ambient temperature and then triturated. The product crystallises out, is filtered off, washed with diethyl ether, dried, and recrystallised from isopropanol, to yield the citrate: ill-defined melting point at 102°–108°C; yield 70%.

Analysis $C_{30}H_{37}NO_{10}$, N% calculated 2.45; found 2.48.

EXAMPLE 3

β-Morpholino-ethyl ester of 2,2-diphenyl-cyclopropane-carboxylic acid

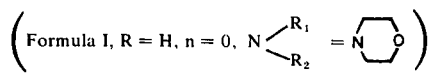

(Formula I, R = H, n = 0, $N\!\!<\!\!^{R_1}_{R_2}$ = $N\!\!\bigcirc\!\!O$)

A solution of 0.1 mol of 2,2-diphenyl-cyclopropane-carboxylic acid chloride in 30 ml. of anhydrous benzene is added dropwise to a mixture of 0.1 mol of β-morpholino-ethanol and 0.1 mol of triethylamine in 50 ml. of anhydrous benzene. The mixture is allowed to cool and then stirred for 2 hours at ambient temperature. 300 cc. of water are added, the mixture is extracted with diethyl ether, the extract dried over sodium sulphate, and the solvent removed in vacuo to yield the base.

Preparation of the hydrochloride

A solution of hydrogen chloride in diethyl ether is added dropwise, with stirring, to a solution of crude base in 100 ml. of diethyl ether, until pH 1 is reached. The mixture is triturated, and the product crystallises; it is filtered off, washed with diethyl ether and recrystallised from isopropanol to yield the hydrochloride: melting point 150°–152°C; yield 76%.

Analysis $C_{22}H_{26}ClNO_3$, N% calculated 3.61; found 3.62.

Other compounds having the general formula I were also prepared by the procedures described in the above Examples; these compounds are listed in Table I below.

TABLE I

| Formula I Example No. | R | $N\!\!<\!\!^{R_1}_{R_2}$ | n | Method of working | Yield, % | Derivative | Crystallisation solvent | Melting point °C | Analysis | |
|---|---|---|---|---|---|---|---|---|---|---|
| 4 | H | dimethyl-amino | 0 | Example 1 | 60 | hydrochloride | isopropanol | 135 | N% calculated | 4.05 |
| | | | | Example 2 | 74 | | | | found | 4.02 |
| | | | | Example 3 | 72 | | | | | |
| 5 | H | pyrroli-dino | 0 | Example 1 | 63 | hydrochloride | isopropanol | 164–5 | N% calculated | 3.77 |
| | | | | Example 2 | 70 | | | | found | 3.76 |
| | | | | Example 3 | 78 | | | | | |
| 6 | H | piperi-dino | 0 | Example 1 | 78 | hydrochloride | isopropanol | 178–80 | N% calculated | 3.63 |
| | | | | Example 2 | 77 | | | | found | 3.67 |
| | | | | Example 3 | 79 | | | | | |
| 7 | H | perhydro-azepino | 0 | Example 1 | 59 | hydrochloride | ethanol | 200–2 | N% calculated | 3.50 |
| | | | | Example 2 | 63 | | | | found | 3.49 |
| | | | | Example 3 | 75 | | | | | |
| 8 | H | morpho-lino | 0 | Example 1 | 62 | hydrochloride | methyl ethyl ketone | 150–2 | N% calculated | 3.61 |
| | | | | Example 2 | 74 | | | | found | 3.62 |
| | | | | Example 3 | 76 | | | | | |
| 9 | H | N-methyl-piperazino | 0 | Example 1 | 57 | dihydro-chloride | ethanol | 202 | N% calculated | 6.39 |
| | | | | Example 2 | 76 | | | | found | 6.36 |
| | | | | Example 3 | 74 | | | | | |
| 10 | H | 3'-methyl-piperidino | 0 | Example 3 | 65 | hydrochloride | isopropanol | 190 | N% calculated found | 3.50 3.49 |
| 11 | H | 4'-methyl-piperidino | 0 | Example 3 | 77 | hydrochloride | isopropanol | 192 | N% calculated found | 3.50 3.55 |
| 12 | H | 2'6'-dimethyl-piperidino | 0 | Example 3 | 45 | hydrochloride | isopropanol | 184 | N% calculated found | 3.38 3.20 |
| 13 | p-CH₃ | pyrrolidino | 0 | Example 3 | 58 | maleate | isopropanol ethyl acetate | 162 | N% calculated found | 2.92 2.89 |
| 14 | p-CH₃ | piperidino | 0 | Example 3 | 63 | maleate | ethyl acetate | 131 | N% calculated found | 2.73 2.80 |
| 15 | p-Cl | piperidino | 0 | Example 3 | 69 | hydrochloride | isopropanol | 163 | N% calculated found | 3.08 3.20 |
| 16 | p-CH₃ | piperidino | 0 | Example 3 | 76 | oxalate | methanol | 173 | N% calculated found | 2.80 2.69 |
| 17 | H | pyrroli-dino | 1 | Example 2 | 70 | citrate | iso-propanol | 102–8* | N% calculated found | 2.45 2.48 |
| | | | | Example 3 | 72 | oxalate | iso-propanol | 134 | N% calculated found | 2.98 2.87 |
| 18 | H | piperi-dino | 1 | Example 2 | 69 | citrate | iso-propanol | 105–10* | N% calculated found | 2.39 2.34 |
| | | | | Example 3 | 75 | | | | | |
| 19 | H | perhydro-azepino | 1 | Example 2 | 71 | hydro-chloride | ethyl acetate | 119 | N% calculated found | 3.15 3.15 |
| | | | | Example 3 | 72 | | | | | |
| 20 | H | N-methyl-piperazino | 1 | Example 2 | 68 | dihydro-chloride | iso-propanol | 170 | N% calculated found | 5.82 5.76 |
| | | | | Example 3 | 76 | | | | | |

*Pasty melting

The pharmacological properties of the esters of 2,2-diphenyl-cyclopropane-carboxylic acid and of their addition salts with non-toxic acids are demonstrated in the following tests, which were carried out on SPF rats and mice, on guinea pigs and on cats.

The products tested are dissolved in a 9% sodium chloride solution or, if they are insoluble in this solution, suspended using "Tween 80" (for oral and intraperitoneal administration) or dissolved in polyethylene glycol 300 (for intravenous administration).

The volumes administered are

| | |
|---|---|
| Rat | 1 ml./kg. |
| Mouse | 0.5 ml./20 g. |
| Guinea Pig | 1 ml./kg. |
| Cat | 1 ml./kg. |

1. Acute toxicity

The acute toxicity is determined on batches, each of two rats. The doses administered extend from 4 to 512 mg./kg. in geometrical progression, constant ratio 2.

Table II below gives the 0 to 100 (%) lethal doses, two days after treatment, in mg./kg. administered intraperitoneally.

TABLE II

| Compound of Example No. | $LD_0$ | $LD_{100}$ |
|---|---|---|
| 1 and 6 | 64 | 128 |
| 2 and 17 | 32 | 128 |
| 3 and 8 | 128 | 256 |
| 4 | 128 | 256 |
| 5 | 128 | 256 |
| 7 | 64 | 128 |
| 9 | 64 | 128 |
| 10 | 64 | 256 |
| 11 | 64 | 256 |
| 12 | 32 | 128 |
| 13 | 128 | 256 |
| 14 | 256 | 512 |
| 15 | 128 | 256 |
| 16 | 128 | 512 |
| 18 | 64 | 256 |
| 19 | 64 | 128 |
| 20 | 64 | 128 |

2. Anti-tussive activity: Domenjoz method

Cats are anaesthetised by intraperitoneal injection of 30 mg./kg. of sodium mebubarbital. The arterial pressure is measured on the femoral artery by a Statham P 23 Db gauge. A tracheotomy is carried out; a Y-shaped cannula allows a part of the air breathed out to be branched off onto a Statham PM 6 gauge; the cardiac rhythm is measured by integration of the QRS complexes of the electrocardiogram. All these measurements are amplified and recorded on a Beckman Dynograph. The two upper laryngeal nerves are very carefully dissected and stimulated for 10 seconds by a surging current generated by a Hugo Sachs Stimulator I: voltage 3 volts, duration 50 minutes, frequency 50 cycles/second. The test products are injected into the femoral vein. The first stimulation takes place 5 minutes after administration of the product and then every 5 minutes until the reaction returns to the initial amplitude. Each nerve is stimulated in turn (left-hand nerve: 5, 15, 25 minutes etc; right-hand nerve 10, 30, 40 minutes etc. after treatment).

The intravenous administration of 1 to 2 mg./kg. of codeine phosphate reversibly inhibits the reaction to the stimulation.

Table III below shows the activity of the products, defined as follows:
0 inactive
+ marked diminution of cough
++ suppression of cough for 5 to 15 minutes
+++ suppression of cough for more than 15 minutes

TABLE III

| Compound of Example No. | Rating |
|---|---|
| 1 and 6 | +++ |
| 2 and 17 | + |
| 3 and 8 | + |
| 4 | + |
| 5 | ++ |
| 7 | ++ |
| 9 | + |
| 10 | ++ |
| 11 | + |
| 12 | ++ |
| 13 | ++ |
| 14 | ++ |
| 15 | + |
| 16 | + |
| 18 | ++ |
| 19 | + |
| 20 | + |

3. Antalgic activity

The products to be tested are administered orally to batches of six mice each weighing 19–21 g. One hour afterwards, 0.20 ml. of an aqueous-alcoholic solution containing 0.02% of phenylbenzoquinone (phenylbenzoquinone: 20 mg; 96% alcohol; 5 ml; water q.s.p. 100 ml) is injected intraperitoneally. The number of reactions (stretching of the body) from the 5th to the 10th minutes following the injection of phenylbenzoquinone is counted.

Table IV gives the percentage inhibition relative to control animals.

TABLE IV

| Dose, mg/kg administered orally | Compound of Example No. | | | | | | | | | | | | | | | |
|---|---|---|---|---|---|---|---|---|---|---|---|---|---|---|---|---|
| | 1 and 6 | 2 and 17 | 3 and 8 | 4 | 5 | 7 | 9 | 10 | 11 | 12 | 13 | 14 | 15 | 16 | 18 | 19 | 20 |
| 16 | 10 | 57 | — | 23 | — | 25 | 14 | 21 | 22 | 45 | 24 | 35 | 29 | 40 | 43 | 3 | 26 |
| 32 | — | 38 | 37 | — | 0 | — | — | — | — | — | — | — | — | — | — | — | — |
| 64 | 31 | 63 | — | 17 | — | 25 | 19 | 46 | 38 | 36 | 24 | 38 | 29 | 28 | 55 | 26 | 38 |
| 128 | — | — | 41 | — | 19 | — | — | — | — | — | — | — | — | — | — | — | — |

4. Local anaesthetic activity

This is investigated by the technique of Bulbring and Wajda. The backs of male guinea pigs weighing 350–450 g. are shaved with an electric razor. 0.1 ml. of a solution of the compounds to be tested is injected into the dermis (only those products which are soluble in the sodium chloride solution and give a pH of 6 to 7 are examined). Four points spaced 2 cm apart are marked on the skin, the product being administered at two of these and the solvent being administered at the remaining two. The skin reflex is examined by pricking each point six times with a mounted bristle. The number of positive reactions is counted and an inhibition percentage is calculated from the total number of positive reactions over the course of 30 minutes. Table V gives the inhibition percentages measured as a function of the concentrations of the solutions. The compounds of Examples 7, 18 and 19 are insoluble under the experimental conditions.

TABLE V

| Compound | Concentration 0/00 0.25 | 0.50 | 1 |
|---|---|---|---|
| Example 1 and 6 | 14 | 32 | 64 |
| Example 2 and 17 | — | 0 | 19 |
| Example 3 and 8 | — | 0 | 26 |
| Example 4 | 68 | 87 | 97 |
| Example 5 | 84 | 81 | 97 |
| Example 9 | — | 0 | 35 |
| Example 10 | — | 36 | 62 |
| Example 11 | 18 | 49 | 81 |
| Example 12 | 49 | 78 | 89 |
| Example 13 | — | 31 | 32 |
| Example 14 | — | 34 | 40 |
| Example 15 | — | 26 | 38 |
| Example 16 | — | 0 | 46 |
| Example 20 | — | 0 | 0 |

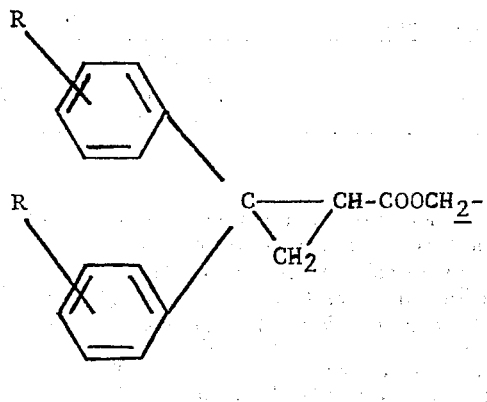

Clinical experiments were also carried out with the product of Example 1 on subjects suffering from chronic bronchitis. Not only suppression of the cough, but also facilitation of expectoration, and even a reduction in the latter and a sensation of feeling better, were observed.

The compounds of formula I can be administered orally at a dose of 50 to 600 mg. daily.

Formulation for gelatine-coated pills

Gelatine-coated pills containing 50 mg. of the compound of Example 1, to be administered at the rate of 1 to 6 gelatine-coated pills daily, taken in 1 to 3 doses.

Formulation of a syrup

| Compound of Example 1 | 100 mg. |
|---|---|
| Flavoured syrup | 100 ml. | to be administered at the rate of 100 to 300 mg. daily, in 1 to 3 doses.

Formulation for suppositories

| Compound of Example 1 | 100 mg. |
|---|---|
| Cacao butter, q.s.p. | 2 g. | to be administered at the rate of 1 to 3 suppositories daily.

The invention thus includes within its scope pharmaceutical compositions comprising, in association with a compatible pharmaceutical carrier, at least one compound of formula I or non-toxic acid addition salt thereof, preferably in a form for oral administration such as a tablet, sugar-coated pill, gelatine-coated pill, or syrup.

I claim:

1. A cough-suppressing composition comprising (1) an effective, non-toxic amount of an ester of a 2,2-diphenylcyclopropane-carboxylic acid of the formula:

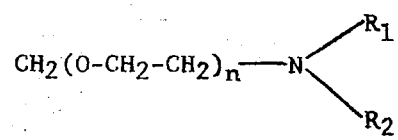

in which R is hydrogen, halogen, lower alkyl, or lower alkoxy, $n$ is zero or 1, and $R_1$ and $R_2$ taken together form, with the nitrogen to which they are attached, piperidino or lower alkyl-substituted piperidino; or a non-toxic acid addition salt of said ester and (2) a pharmaceutically acceptable excipient.

2. A pharmaceutical composition according to claim 1 in which the active ingredient is the β-piperidinoethyl ester of 2,2-diphenyl-cyclopropanecarboxylic acid.

3. A pharmaceutical composition according to claim 1 in which the active ingredient is the β-(4'-methylpiperidino)ethyl ester of 2,2-diphenylcyclopropanecarboxylic acid.

4. A pharmaceutical composition according to claim 1 in which the active ingredient is the β-(2',6'-dimethyl-piperidino)ethyl ester of 2,2-diphenyl-cyclopropanecarboxylic acid.

5. A pharmaceutical composition according to claim 1 in which the active ingredient is the β-piperidinoethyl ester of 2,2-di-(p-methyl-phenyl)-cyclopropanecarboxylic acid.

6. A pharmaceutical composition according to claim 1 in which the active ingredient is the 2-(2'-piperidinoethoxy)-ethyl ester of 2,2-diphenyl-cyclopropanecarboxylic acid.

7. The pharmaceutical composition of claim 1 in a form suitable for oral administration.

8. The pharmaceutical composition of claim 1 suitable for administration as a suppository.

9. A method of suppressing cough which comprises administering to a subject suffering therefrom an effective, non-toxic amount of an ester of a 2,2-diphenyl-cyclopropanecarboxylic acid of the formula:

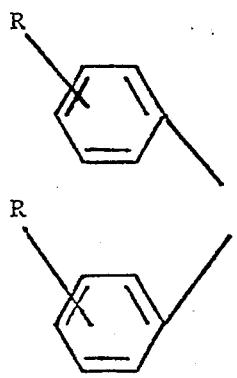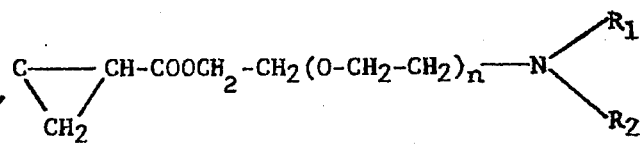

in which R is hydrogen, halogen, lower alkyl, or lower alkoxy, n is zero or 1, and $R_1$ and $R_2$ taken together form, with the nitrogen to which they are attached, piperidino or lower alkyl-substituted piperidino; or a non-toxic acid addition salt of said ester.

10. The method of claim 9 wherein said ester is the β-piperidinoethyl ester of 2,2-diphenyl-cyclopropanecarboxylic acid.

11. The method of claim 9 wherein said ester is the β-(4'-methyl-piperidino)-ethyl ester of 2,2-diphenyl-cyclopropanecarboxylic acid.

12. The method of claim 9 wherein said ester is the β-(2',6'-dimethyl-piperidino) ethyl ester of 2,2-diphenyl-cyclopropanecarboxylic acid.

13. The method of claim 9 wherein said ester is the β-piperidinoethyl ester of 2,2-di-(p-methylphenyl)-cyclopropanecarboxylic acid.

14. The method of claim 9 wherein said ester is the 2-(2'-piperidino-ethoxy)-ethyl ester of 2,2-di(p-methyl-phenyl)-cyclopropanecarboxylic acid.

* * * * *